United States Patent [19]

Goble et al.

[11] Patent Number: 5,352,229
[45] Date of Patent: Oct. 4, 1994

[54] ARBOR PRESS STAPLE AND WASHER AND METHOD FOR ITS USE

[76] Inventors: E. Marlowe Goble, 850 E. 1200 North; David P. Luman, 1430 E. 1260 North, both of Logan, Utah 84321

[21] Appl. No.: 59,618

[22] Filed: May 12, 1993

[51] Int. Cl.$^5$ ............................................. A61F 5/04
[52] U.S. Cl. ..................................... 606/72; 606/73; 606/75; 606/220
[58] Field of Search ...................... 606/72, 73, 75, 76, 606/77, 219, 220; 411/921, 451, 455, 457, 480

[56] References Cited

U.S. PATENT DOCUMENTS

| D. 280,550 | 9/1985 | Pratt et al. |
| D. 281,814 | 12/1985 | Pratt et al. |
| D. 284,509 | 7/1986 | Johnson. |
| 82,181 | 9/1868 | Tileston. |
| 431,175 | 7/1890 | Southwick. |
| 758,881 | 5/1904 | Yost. |
| 1,425,199 | 8/1922 | Hartley. |
| 1,598,026 | 8/1926 | Thompson. |
| 1,638,477 | 8/1927 | Dyer. |
| 1,948,462 | 12/1936 | Le Page. |
| 2,134,765 | 11/1938 | Putnam. |
| 2,398,603 | 4/1946 | Soderberg. |
| 2,919,621 | 1/1960 | Langdon. |

(List continued on next page.)

FOREIGN PATENT DOCUMENTS

| 0033641B1 | 8/1981 | European Pat. Off. |
| 0406014A1 | 1/1991 | European Pat. Off. |
| 0488906A1 | 6/1992 | European Pat. Off. |
| 0495673 | 7/1992 | European Pat. Off. ............ 606/220 |
| 0520177A1 | 12/1992 | European Pat. Off. |
| 1558965 | 1/1980 | United Kingdom. |

OTHER PUBLICATIONS

WO 90/00370 PCT Application.
Linvatec Catalog-pp. 77 and 81-Spiked Washers and Fixation Staples, 1992.
Zimmer Catalog-pp. B88, B89, B90, B91, C57-Staples and Washers-1987.
Synthes Catalog-p. 44-Spiked Washer-1977 (Also related Synthes Bulletin).
Manual of Internal Fixation-p. 29-Washers-1979.
Howmedica catalog-pp. D107, D108, E15, F28-Staples-1978.
Howmedica catalog-p. G33-I.C.L.H. Staple System-1984.
Howmedica ad-Ellison Staply-JBJS-Oct. 1986.

Primary Examiner—Stephen C. Pellegrino
Assistant Examiner—Sonya C. Harris
Attorney, Agent, or Firm—M. Reid Russell

[57] ABSTRACT

An arbor press staple and washer of the invention is for use in a practice of a surgical procedure for securing a ligament, that is either natural or prosthetic, onto a bone cortex surface and includes a staple having spaced equal parallel legs with a flat web arranged between the top ends of the staple legs. The staple is for driving into a bone cortex surface and includes barb ridges around three of its four sides for resisting staple withdrawal. The staple flat web includes at least one hole, that is preferably tapped, formed therethrough that is for receiving a threaded section of a threaded pin turned therethrough, and includes a pair of guide posts that extend, at right angles, from the web undersurface. An arbor plate type washer, that is a flat plate that has concave notches formed in opposite ends, is for arrangement between the staple legs, the concave notches sliding along the staple legs prohibiting washer rotation. The flat plate includes a pair of guide post holes that receive the guide pins that extend from the staple web undersurface, and includes a center smooth hole wherethrough a pin end of the threaded pin travels to where the threaded section lower face and engages the flat plate top surface, the continued turning of the threaded pin to urge the washer away from the staple web, causing spikes that extend from the washer flat plate undersurface to travel through a ligament that the staple legs straddle and into a bone cortex surface.

22 Claims, 2 Drawing Sheets

U.S. PATENT DOCUMENTS

| | | |
|---|---|---|
| 4,047,524 | 9/1977 | Hall . |
| 4,146,022 | 3/1979 | Johnson et al. . |
| 4,263,903 | 4/1981 | Griggs . |
| 4,263,903 | 4/1981 | Griggs . |
| 4,278,091 | 7/1981 | Borzone ............................ 606/219 |
| 4,400,833 | 8/1983 | Kurland . |
| 4,414,967 | 11/1983 | Shapiro . |
| 4,438,769 | 3/1984 | Pratt et al. . |
| 4,454,875 | 6/1984 | Pratt et al. . |
| 4,456,006 | 6/1984 | Wevers et al. . |
| 4,462,395 | 7/1984 | Johnson . |
| 4,548,202 | 10/1985 | Duncan . |
| 4,570,623 | 2/1986 | Ellison et al. . |
| 4,590,928 | 5/1986 | Hunt et al. . |
| 4,592,346 | 6/1986 | Jurgutis . |
| 4,607,638 | 8/1986 | Crainich . |
| 4,632,100 | 12/1986 | Somers et al. . |
| 4,655,222 | 4/1987 | Florez et al. . |
| 4,659,604 | 4/1987 | Lambuth . |
| 4,711,234 | 12/1987 | Vives et al. . |
| 4,723,540 | 2/1988 | Gilmer, Jr. . |
| 4,738,255 | 4/1988 | Goble et al. . |
| 4,759,765 | 7/1988 | Van Kampen . |
| 4,793,335 | 12/1988 | Frey et al. . |
| 4,834,752 | 5/1989 | Van Kampen . |
| 4,838,254 | 6/1989 | Gauthier . |
| 4,848,328 | 7/1989 | Laboureau et al. . |
| 4,852,558 | 8/1989 | Outerbridge . |
| 4,913,144 | 4/1990 | Del Medico . |
| 4,955,899 | 9/1990 | Matsutani et al. . |
| 4,960,420 | 10/1990 | Goble et al. . |
| 4,988,351 | 1/1991 | Paulos et al. .......................... 606/72 |
| 5,013,316 | 5/1991 | Goble et al. . |
| 5,053,038 | 10/1991 | Sheehan . |
| 5,129,902 | 7/1992 | Goble et al. . |
| 5,167,665 | 12/1992 | McKinney . |
| 5,209,756 | 5/1993 | Seedhom et al. . |

ARBOR PRESS STAPLE AND WASHER AND METHOD FOR ITS USE

BACKGROUND OF THE INVENTION

1. Field of the Invention

This invention relates to devices and arrangements for securing a ligament, or the like, onto a bone surface during a ligament repair or replacement surgical procedure.

2. Prior Art

One of the present inventors is the co-inventor of an earlier invention entitled, Channel Ligament Clamp and System, U.S. Pat. No. 4,960,420, and a U.S. Patent Application entitled, Improved Channel Ligament Clamp, U.S. Ser. No. 07/959,546, that show arrangements of clamping devices for mounting a ligament onto a bone surface. Which channel ligament clamps, like the present invention, employ a flat ligament engaging surface, wherefrom a plurality of spikes extend to penetrate the ligament and pass into the bone surface providing purchase therewith. Unique therefrom, the present invention provides, as a reference, a staple arrangement with parallel legs for driving into a bone surface, to straddle a ligament, with a movable arbor plate type washer wherefrom spikes extend arranged to travel between the staple legs through a ligament and into the bone surface. For moving the arbor plate type washer, the staple web is flattened and has a tapped hole formed therethrough that a threaded pin is turned into. The pin has a pointed end that when it is turned through the tapped hole, travels into a center hole that has been formed in the arbor plate type washer, a flat section above the pin top end urging that arbor plate type washer away from the staple web forcing the arbor plate type washer spikes through a ligament that the staple legs straddle and into the bone cortex.

Additional to the above cited channel ligament clamp type systems, staple arrangements that do not include the movable arbor plate type washer, have been earlier employed in ligament repair and replacement surgical procedures for attaching a ligament to a bone surface. Examples of such staple devices for medical applications are shown in patents to Hall, U.S. Pat. No. 4,047,524; to Johnson, et al, U.S. Pat. No. 4,146,022; to Griggs, U.S. Pat. No. 4,263,903; to Borzone, U.S. Pat. No. 4,278,091; to Kurland, U.S. Pat. No. 4,400,833; to Shapiro, U.S. Pat. No. 4,414,967; to Pratt, et al, U.S. Pat. No. 4,438,769; and to Wevers, et al, U.S. Pat. No. 4,456,006. All of which staple devices provide for fitting the staple like device across the ligament to secure the ligament between the staple legs by driving it into the bone surface. None of these staple devices, however, employ a movable spike mounting arbor plate type washer like that of the present invention, and an arrangement for moving the spikes of that arbor plate type washer into a ligament that is independent of movement of the staple, as does the present invention. Also, while a number of staple and staple like devices are common to wood working, none employ the movable arbor plate type washer arrangement like that of the present invention, and are additionally structurally and functionally unlike the present invention. Some examples of wood working type staple like devices are shown in early patents to Tileston, U.S. Pat. No. 82,181; to Southwick, U.S. Pat. No. 431,175; to Yost, U.S. Pat. No. 758,881; to Hartley, U.S. Pat. No. 1,425,199; to Thompson, U.S. Pat. No. 1,598,026; to Dyer, U.S. Pat. No. 1,638,477; to Le Page, U.S. Pat. No. 1,948,462; to Putnam, U.S. Pat. No. 2,134,765; to Soderberg, U.S. Pat. No. 2,398,603; and in a later patent to Lambuth, U.S. Pat. No. 4,659,604.

Some examples of other devices for connecting ligament ends to a bone surface or within a bone are shown in a patent to Hunt, et al, U.S. Pat. No. 4,590,928 and in patents that one of the present inventors is the co-inventor of, U.S. Patent Nos. 4,632,100 and 4,738,255. Further patents to Vives, et al, U.S. Pat. No. 4,711,234 and to Paulos, et al, U.S. Pat. No. 4,988,351, show, respectively, pin and disk couplings for ligament mounting to a bone mass. Also, devices for mounting a ligament onto a bone surface are shown in patents to Jurgutis, U.S. Pat. No. 4,592,346 and to Frey, et al, U.S. Pat. No. 4,793,335 that show multi-pin staple arrangements.

None of which connector and mounting configurations, set out above, however, involve a staple with a spike mounting arbor plate type washer that is arranged to be vertically movable, guided by the staple legs, that includes with the staple legs seated in a bone surface an arrangement for moving the arbor plate type washer so as to clamp a ligament onto the bone surface.

BRIEF SUMMARY OF THE INVENTION

It is a principal object of the present invention in an arbor press staple and washer to provide a combination of a staple for driving into a bone cortex, straddling a ligament, and a movable arbor plate type washer with spikes extending therefrom that is arranged between the staple legs to travel into to secure the ligament onto the bone cortex.

Another object of the present invention is to provide an arbor press staple and washer where the staple parallel legs are pointed and include ridge barbs formed at spaced at intervals thereacross for binding in the bone when the staple is driven into the bone cortex.

Another object of the present invention is to provide an arbor press staple and washer where the staple web is a flattened section wherethrough at least one hole is formed that receives a section of a pin fitted therethrough, a pin end thereof engaging the washer to urge it away from the staple web to where the washer spikes travel into a ligament that the staple legs straddle.

Another object of the present invention is to provide an arbor press staple and washer where the washer is guided away from the staple web undersurface so as to remain essentially parallel to the web undersurface as the pin section moves the washer such that its spikes travel into the ligament.

Another object of the present invention is to provide an arbor press staple and washer where the pin section is threaded and includes a pin pointed end arranged below a threaded section, the pin pointed end to slide through a center hole formed in the washer, parallel to the arbor plate spikes, to where the threaded section lower face engages the arbor plate type washer, urging it away from the staple web undersurface.

Another object of the present invention is to provide an arbor press staple and washer that is formed of a human body compatible material and is easy and reliable to use for securing a ligament onto a bone cortex surface.

Still another object of the present invention is to provide a method utilizing an arbor press staple and washer for exactly mounting a ligament onto a bone surface that is also capable of performing a self jacking function for lifting staple legs out of a bone cortex wherein the legs have been driven for removal of the staple.

The arbor press staple and washer of the present invention includes a staple preferably having equal parallel legs that are each pointed on lower ends thereof. Each staple leg includes spaced ridge barbs formed at intervals thereacross around three of four sides, for driving into a bone cortex, the ridge barbs discouraging staple withdrawal. The staple includes a wide flat web between top ends of the staple legs that includes at least one hole that is preferably centered and a center tapped formed therethrough, the hole or holes each for receiving a shaft fitted therethrough to engage and force a flat plate type washer along the staple legs, away from the staple web. The shaft may be arranged to be a snap-in spring loaded, or the like, but preferably involves a threaded section formed around an upper section of a threaded pin that is turned through the hole that has been threaded. The threaded pin including a sharp pin end extending axially from the bottom face of the threaded section. The flat arbor plate type washer, preferably includes notches formed in its opposite ends, that are fitted between to slide along the staple parallel legs. The arbor plate type washer undersurface includes a plurality of spikes that extend parallel to one another at approximately right angles therefrom at the washer corners and surrounding the hole or holes formed therethrough that receive the pin end fitted therethrough. The staple web undersurface further includes a pair of spaced guide posts that extend at right angles therefrom and are to fit into spaced guide holes formed in the arbor plate type washer. The guide pins for guiding the washer as the threaded section of the pin is turned in the tapped flat web hole, urging the arbor plate washer away from the staple web undersurface, the washer spikes to pass through, a ligament that the staple legs straddle.

To mount a ligament onto a bone cortex surface utilizing the arbor press staple and washer of the invention, the arbor plate type washer is fitted between the staple legs, and the staple, straddling a ligament, is driven into a bone cortex, the ridge barbs of the staple legs binding into the bone to prevent removal of the staple legs from the bone cortex. Whereafter, the threaded section of the threaded pin is turned into each tapped hole that has been formed in the staple web, the pin pointed end traveling through a smooth center hole formed in the arbor plate type washer to where the pin extends therethrough. So arranged, an undersurface of the pin threaded section engages the arbor plate type washer top surface around the hole, urging it away from the staple web. The arbor plate type washer is guided along the guide posts, with the arbor plate type washer lower face wherefrom spaced spikes extend and the pin pointed end urged through the ligament and into the bone cortex, mounting it thereto. To release the ligament, the threaded pin can be turned out of the staple web tapped hole, releasing the arbor plate type washer and allowing the washer spikes to be pulled out of the ligament, releasing the ligament to be pulled out from between the staple legs. To remove the staple a threaded shaft is substituted for the threaded pin and is turned against the washer top surface or against the bone itself. Where, with continued shaft turning, the staple legs are jacked out of the bone cortex allowing for staple removal.

DESCRIPTION OF THE DRAWINGS

These and other objects and features of the present invention will become more fully apparent from the following description taken in conjunction with the accompanying drawings.

DETAILED DESCRIPTION

In ligament repair or replacement surgical procedures that involve biologic or prosthetic ligament grafts, a ligament end may be required to be exactly positioned and maintained onto a bone cortex location. Once proper ligament positioning is determined a fastener device is used to attach the ligament end onto that bone surface at the required location, which ligament is usually maintained under tension. The need for exact positioning of a ligament while maintaining proper ligament tensioning is obviously difficult. This difficulty is minimized utilizing the arbor press staple and washer 10 the invention, hereinafter referred to as arbor press staple.

Figure 1:
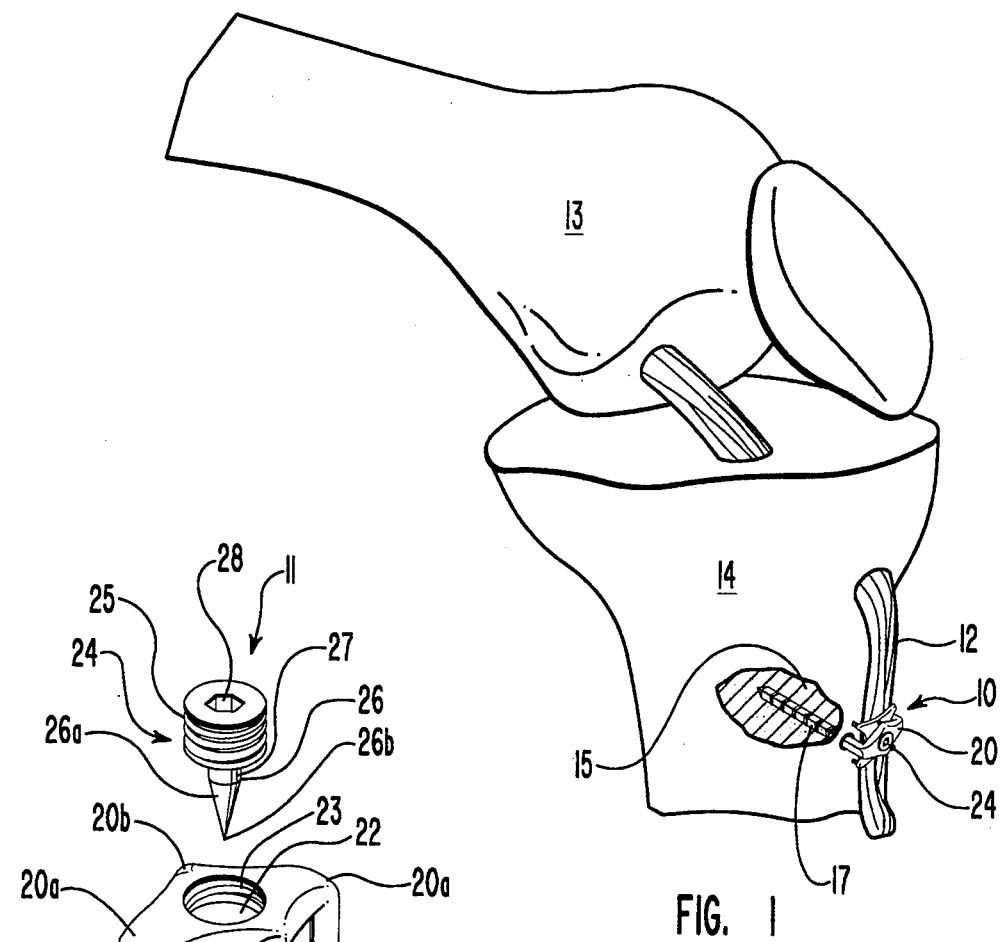
FIG. 1 is a side elevation perspective view of a distal femur and proximal tibia of a patient's knee showing a ligament installed in a straight ligament tunnel that has been formed across the ligament points of origin, with a ligament tibial end shown mounted to the tibial cortex surface utilizing an arbor press staple and washer of the invention.

The arbor press staple 10, is shown in FIG. 1, as mounting a tibial end 12 of a natural ligament 11 onto a tibia 14 surface, the ligament 11 shown endosteally mounted in a femoral tunnel end of a straight ligament tunnel that has been formed into the distal femur 13 and proximal tibia 14, in a cruciate ligament replacement procedure. The ligament tibial end 12 is shown fixed onto the tibia cortex 15. The above set out utilization of the arbor press staple 10 of the invention, it should be understood, is for example only and the invention can be used for many applications where it is required to mount a ligament onto a bone surface.

Figure 2:
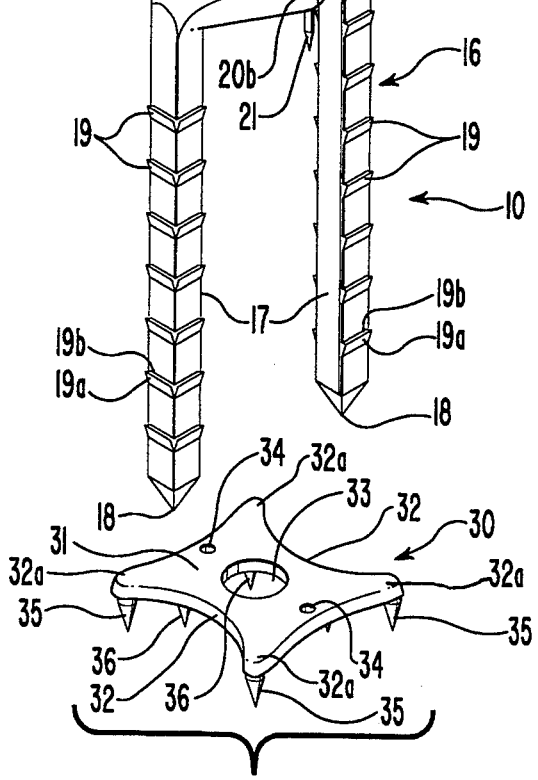
FIG. 2 is an exploded profile perspective view of the arbor press staple and washer of the invention.
Figure 3:
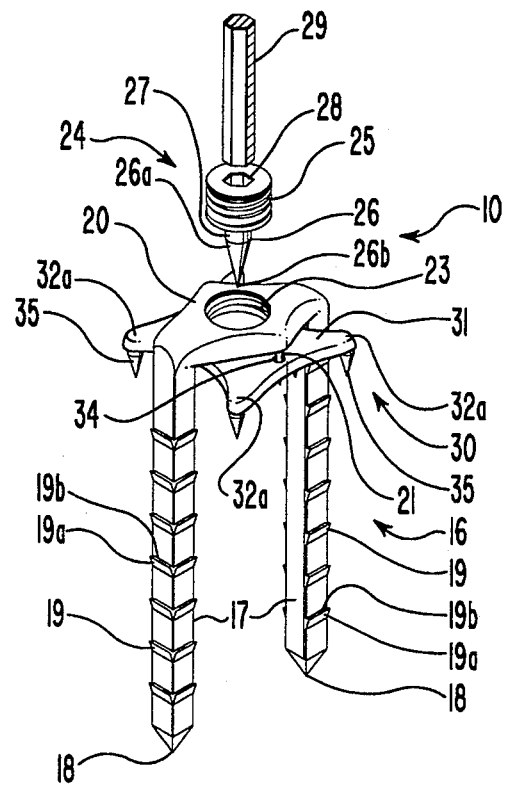
FIG. 3 is an assembled view of the arbor press staple and washer or FIG. 2, showing an end section of an alan wrench fitting into a hexagon sided longitudinal opening in the top surface of a threaded pin that is aligned for turning into a tapped hole formed in the center of a staple flat web.

Shown best in FIGS. 2 and 3, the arbor press staple 10 includes a staple 16 that preferably has a pair of identical parallel straight legs 17, each having a pointed end 18, and each having a number of barb ridges 19 that are formed across the three sides of the four sides of staple legs, at spaced intervals therealong. Each of the barb ridges 19 extends around all but the opposing faces of the staple legs 17, and has a face 19a that slopes outwardly from a contact with the staple surface and upwardly from the staple pointed ends 18. A right angle or greater leg 19b is shown extending back to the staple surface forming a base leg. The barb ridge sloping surface 19a is to slide into a hole formed into the bone cortex 15 as the staple is driven therein, the bone material flowing around that staple leg, with the barb ridge leg 19b, at its junction with the sloping face 19a, prohibiting staple withdrawal.

The staple 16, includes a flat web 20 secured between the top ends of staple legs 17. The web 20, as shown, has a diamond shape the most distant ends 20a mounting, at right angles, the staple legs 17 to the web undersurface, with guide posts 21 shown extending, at right angles, from the web 20 undersurface, at the diamond proximal ends 20b. The guide posts 21 are for guiding an arbor plate type washer 28 as set out and discussed in detail hereinbelow.

As shown best in FIGS. 2 and 3, the staple web 20 is shown as including a center hole 22 that is formed therethrough though, it should be understood, a plurality of holes could be so formed, each for receiving a pin fitted therein, within the scope of this disclosure. Which center hole 22 is shown as tapped with threads 23. A threaded pin 24 is shown aligned with web center hole 22 for fitting therein. Threads 25 are formed along an upper or top section of the threaded pin for turning into the web center hole threads 23. Turning of the pin threads 25 into the web center hole threads 23 causes a pin 26, that is connected to extend axially from the undersurface of the pin threaded section, to project through the web center hole 22 at a right angle to the web undersurface. Turning of the threaded pin 24 into the web center hole 22 projects the pin 26 downwardly, a sloping surface 26a of the pin 24, from a pointed end 26b upwardly to a cylindrical section for travel into a center opening 33 of an arbor plate type washer 30, as set out hereinbelow. The turning of the thread pin 24 is preferably provided, as shown in FIG. 3, by fitting an end 29 of an Alan Wrench type tool into a sided recess 28 that has been formed into the top surface of the threaded pin 24. The recess 28 is shown to have a hexagon, six sided shape, to accommodate the Alan Wrench type tool end 29 fitted therein. Though, of course, another tool and recess arrangement could be so used within the scope of this disclosure. One such arrangement could be a screw driver with a straight slot formed across the threaded pin top surface, or the like. Also, while the arrangement of the threaded pin 24 for turning in threaded center hole 23 is preferred it should be understood that other arrangements for extending a shaft or pin from the undersurface of the staple web 20 to engage the arbor press type washer could be utilized within the scope of this disclosure. For example, a non-threaded snap-on pin and hole arrangement or a spring loaded shaft, not shown, could be so used within the scope of this disclosure and, as set out above, plurality or pins and holes formed through the staple web 20 can be utilized, as required.

Shown in FIGS. 2 and 3, an arbor plate type washer 30, hereinafter referred to as washer, is positioned, as shown in FIG. 2, to slide vertically between the staple legs 17, to the attitude shown in FIG. 3. As shown, the washer 30 consists of a flat plate 31 that includes a center smooth wall opening 33 formed therethrough that is of a diameter to allow the threaded pin 24 pointed end 26b and sloping portion 26a to pass therethrough, along with the pin 26 cylindrical section 27, to where the threaded portion 25 undersurface rests on the washer 31 surface around opening 33. With continued turning of the threaded pin 24, the flat plate 31 slides down the staple legs 17. To maintain the washer between the staple legs, the washer includes arcuate notches 32 formed in opposite sides of the flat plate 31. So arranged, the washer flat plate surface between the notches 32 is to fit between the staple legs, the flat plate corners 32a extending beyond the staple legs, for prohibiting washer 30 rotation. Additional to the notches 32, for stabilizing the washer between staple legs 17, the flat plate 31 includes guide post holes 34 that are formed therethrough for receiving the guide posts 21 that extend from the staple web 20 undersurface. The washer 30 is to slide along the guide posts as the threaded pin 24 is turned into staple web center hole 22, as shown in FIGS. 4 and 5.

Figure 4:
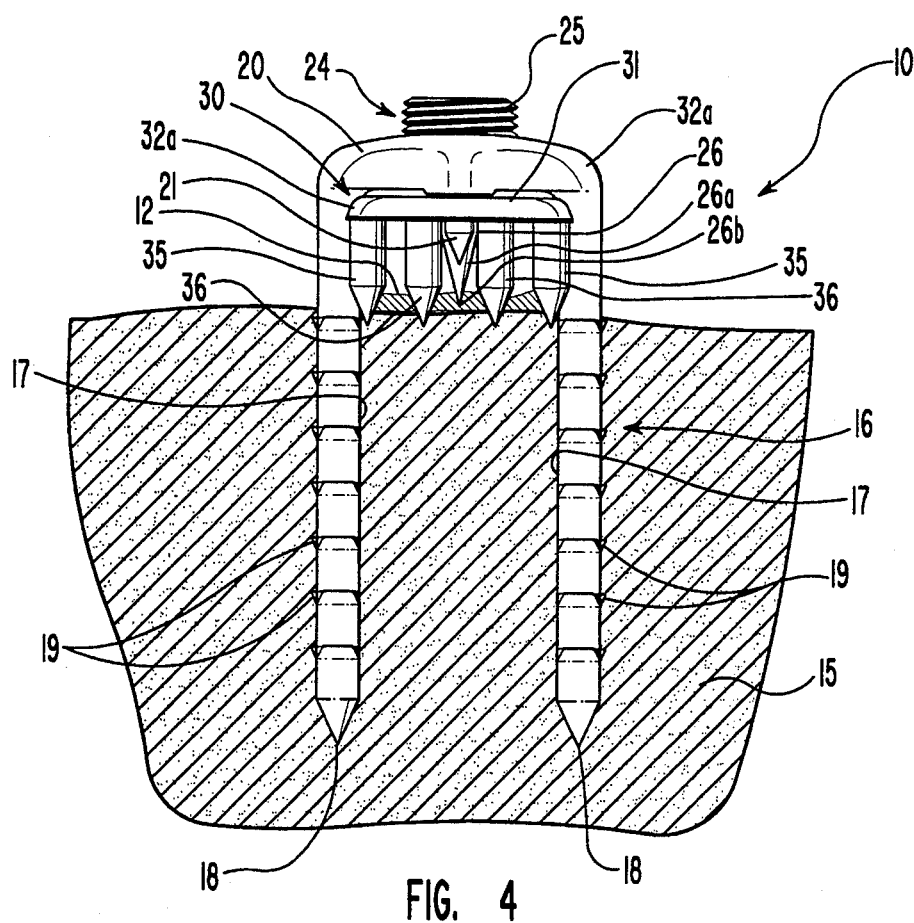
FIG. 4 is a side elevation view of the arbor press staple and washer of FIG. 3 with the staple legs shown driven into a bone cortex.
Figure 5:
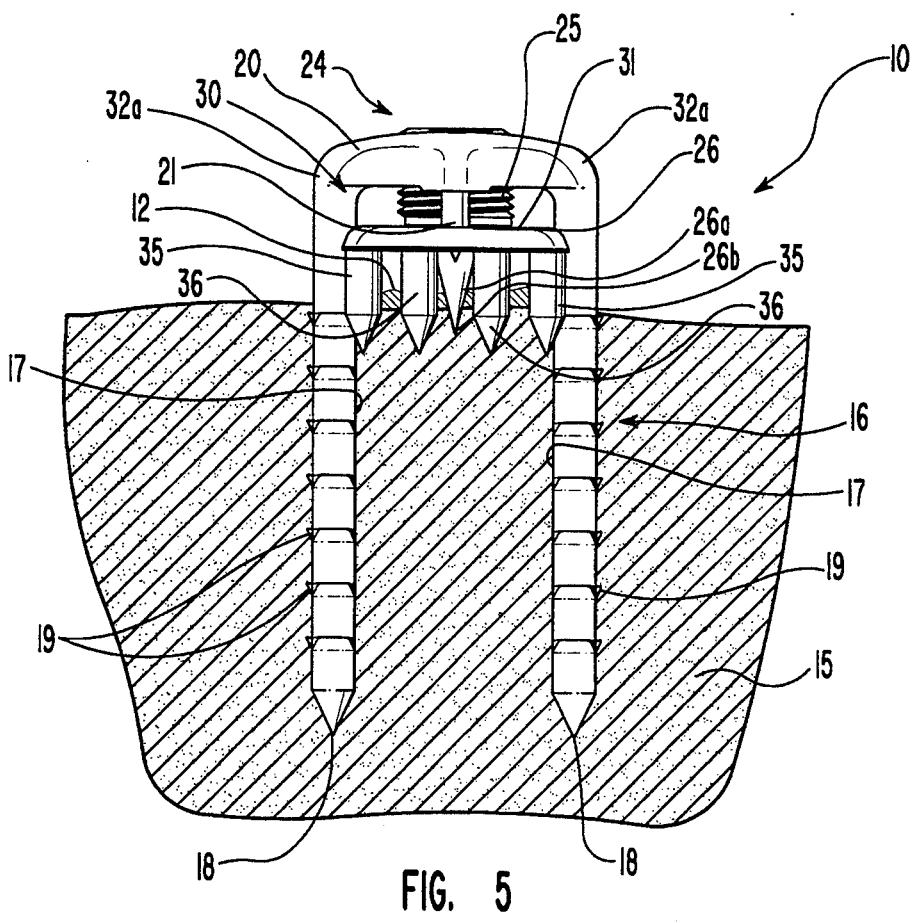
FIG. 5 is a view like FIG. 4, showing the threaded pin as having been turned into the staple web tapped hole, urging the arbor plate type washer spikes into the bone cortex.

For engaging and mounting a ligament end 12 onto a bone cortex 15 utilizing the arbor press staple 10, as shown in FIGS. 4 and 5, the undersurface of the washer flat plate 31 includes a plurality of straight spikes that extend at right angles therefrom. Shown in FIGS. 2 through 5, the straight spikes include corner spikes 35 and a square of spikes 36 that are arranged at equal intervals around the flat plate 31 center opening 33. The spikes 35 and 36 along with the pin 26, as shown, are to travel into and through the ligament end 12 and may travel into the bone cortex 15 for ligament end mounting so as to provide a mounting that has a strong purchase. Of course, as the arbor press staple 10 is for human implantation it must be formed of a human compatible material such as a stainless steel, or other suitable material.

In practice, for mounting a ligament onto bone surface, the staple 16 is positioned over a location on the bone surface whereto a ligament is to be fixed. Which positioning may involve mounting a positioning tool, not shown, to the staple web 20 for use in directing the staple legs pointed ends 18 to a desired location on the bone, so as to straddle a ligament end 12 to be fixed thereto. Such tool can be a driver for receiving a hammer blow on one end that is transmitted into the staple, driving the pointed ends 18 of staple legs 17 into the bone cortex, and can provide for mounting to the staple web as by turning a component of that tool into the threads 23 of the web center hole 22, facilitating staple positioning. Prior to driving which staple 16 into the bone cortex 15, the washer 30 is fitted between the staple legs 17 such that the washer flat plate 31 arcuate notched sides 32 will slide along the staple legs.

The staple 16 is driven into the bone cortex 15 to provide a desired spacing of the arbor plate spikes 35 and 36 ends above the bone surface. The spikes 35 and 36 that extend from the bottom surface of which fixed plate are to travel into the ligament end 12 that has been positioned between the staple legs 17, and may travel into the location on the bone surface. Further, for guiding the movement of the washer 30, the staple web 20 undersurface includes the pair of spaced guide posts 21 that align to fit into guide post holes 34 that are formed in the washer flat plate 31, the guide posts 21 to slide therealong as the washer 30 is moved vertically. To provide washer movement, as set out above, the threaded pin 24 threaded end 25 is turned into the threads 23 of web center hole 22, projecting the pin 26 downwardly from the staple web, into a smooth flat plate center hole 33. The pin 26 is to travel fully through the web center hole 22 with the lower face of the threaded pin section 25 engaging and urging the washer flat plate 31 away from the staple web 20 undersurface. The washer 30 thereby functions as an arbor press, the threaded pin 24 functioning as a piston to urge the washer away from the staple web 20 towards the bone surface. In which movement the washer flat plate spikes 35 and 36 along with pin 26 travel into and through the ligament end 12 and may travel into the bone cortex 15.

To remove the ligament from the bone cortex 15 the threaded pin 24 may be turned out of the web center hole 22, allowing the washer 30 to be lifted off of the ligament that can then be slid out from under the spikes 35 and 36. For removing the staple 16 from the bone cortex 15, a shaft that is like the threaded pin 24, that includes threads for turning in the web center hole 22 and is somewhat longer, is turned into the center hole 22 to engage the washer 30 with a pointed or blunt end thereof. The washer is thereby urged against the bone cortex and, with continued shaft turning in the staple web threaded center hole 22, the staple web tends to be moved away from the bone cortex pulling or jacking the staple legs 17 out of the bone cortex, allowing the staple to be pulled therefrom.

While a preferred embodiment of the invention in an arbor press staple and washer has been shown and described herein, it should be understood that the present disclosure is made by way of example only and that variations to the described device and its use are possible within the scope of this disclosure without departing from the subject matter coming within the scope of the following claims, and a reasonable equivalency thereof, which claims we regard as our invention.

We claim:

1. An arbor press staple and washer comprising, a staple having a pair of spaced apart legs and including a web section extending between top ends of said staple legs that includes at least one hole formed therethrough; a shaft for fitting through said web section hole; means for controlling and advancing projection of said shaft out from said web section; and an arbor plate for disposition between said staple legs that is formed as a washer that is a thin flat plate, has opposite ends that fit between said staple legs and includes a plurality of spikes that extend from an undersurface.

2. An arbor press staple and washer as recited in claim 1, wherein the web section hole is threaded; the shaft includes an upper portion that is a threaded section for turning in said threaded hole as the means for controlling shaft projection; a tool receiving recess formed in a top surface of said shaft for receiving a tool fitted therein as a means for providing shaft turning; and said shaft includes a pointed pin section that extends axially from a lower face of said threaded section.

3. An arbor press staple and washer as recited in claim 2, wherein the washer is notched along opposite edges to accommodate the staple legs and includes at least one opening formed therethrough for aligning with the shaft pointed section pin and said hole is of a diameter to pass said pointed pin section therethrough, a lower face of the threaded section engaging the a top surface of said washer, around said opening, said shaft pointed pin section extending through said flat plate and alongside the plurality of spikes.

4. An arbor press staple and washer as recited in claim 3, wherein the spikes are arranged at corners of the washer undersurface, and at spaced intervals around the hole or holes.

5. An arbor press staple and washer as recited in claim 1, wherein, each staple leg includes a plurality of spaced barb ridges formed around three sides of each four sided staple leg, with said staple legs opposing surfaces having smooth faces.

6. An arbor press staple and washer as recited in claim 1, wherein the staple legs are of equal length and each has a pointed lower end; and the spaced barb ridges are each formed with a flat outwardly sloping surface that slopes away from said staple leg point lower end and connects along an edge to a flat surface that extends outwardly from the staple leg surface.

7. An arbor press staple and washer as recited in claim 1, further including at least one guide post secured at a right angle from the undersurface of the web section that fits into a guide hole formed through the washer, for guiding said washer along said guide post.

8. A method for mounting a section of a ligament onto a bone cortex utilizing a combination of a staple with a washer disposed between legs of the staple that is moved against a ligament surface comprising the steps of, selecting a location on a bone cortex surface to attach a ligament section to and driving pointed ends of legs of a staple therein such that said staple legs straddle said ligament section positioned thereon and urge a washer disposed between said staple legs to slide against said ligament section; and, fitting a shaft through a hole through a web of said staple, and applying a force through said shaft between said web of said staple and said washer to urge said washer against said ligament section to clamp said ligament section against the bone cortex surface.

9. A method as recited in claim 8 further including, tapping the staple web hole forming threads therein to receive a threaded section of the shaft and turning said shaft therethrough to where an end of said shaft engages the washer and urges it against the ligament section.

10. A method as recited in claim 8, further including guiding travel of the washer along the staple legs into contact with the ligament section.

11. A method as recited in claim 8, further including releasing the ligament section by reversing the force applied through the shaft between the staple web and washer to where said washer can be lifted off of said ligament section.

12. A method as recited in claim 8, further including removing the staple from the bone cortex by applying a force through the shaft between the staple web and washer to urge said washer against the bone cortex surface so as to lift the staple legs out of their seating in said bone cortex surface.

13. An arbor press staple comprising, a staple having a pair of spaced apart legs and including a web section extending between top ends of said staple legs, and said web section includes at least one hole formed therethrough; a shaft for projecting through said hole; and means for controlling projection of said shaft end that travels from said staple web alongside said staple legs.

14. An arbor press staple as recited in claim 13, further including tapping the hole formed through the staple web section; and the shaft includes a threaded section for turning through said staple web section hole as the means for controlling projection of each said shaft end out from said staple web section.

15. An arbor press staple as recited in claim 14, wherein an upper portion of the shaft is threaded for turning in said threaded hole as the means for controlling shaft projection; the shaft end is pointed and a tool receiving recess is formed in a top surface of said shaft for receiving a tool fitted therein for providing shaft turning as the means for controlling projection of said shaft pointed end.

16. An arbor press staple as recited in claim 13, wherein the staple legs are of equal length and each has a pointed lower end; and the barb ridges are each formed with a flat outwardly sloping surface that slopes away from said staple leg lower end and connects along an edge to a flat surface that extends outwardly from the staple leg surface.

17. An arbor press staple and washer for securing soft tissue adjacent to bone comprising, a staple having a pair of spaced apart legs adapted for insertion into bone and including a web section extending between top ends of said staple legs; a movable plate for disposition between said staple legs and adapted to cover soft tissue between said staple legs; and means extending between said staple and said movable plate to bias said movable plate towards said bone.

18. An arbor press staple and washer as recited in claim 17, wherein the movable plate is a thin flat plate arranged to fit between the staple legs and includes a plurality or spikes that extend from a plate undersurface.

19. An arbor press staple and washer as recited in claim 18, wherein the movable plate opposite ends are notched to accommodate the staple legs fitted therebetween.

20. An arbor press staple and washer as recited in claim 17, wherein the staple web includes at least one hole formed therethrough; and the means extending between the staple web and movable plate is a shaft for fitting through said staple web hole and including a means for advancing projection of said shaft out from said staple web.

21. An arbor press staple and washer as recited in claim 20, wherein the staple web hole is threaded as is a portion of the shaft for turning in said staple web threaded hole as the means for advancing projection of said shaft.

22. An arbor press staple and washer as recited in claim 21, further including at least one hole formed through the movable plate that aligns with the threaded hole formed through the staple web; and said shaft upper portion is threaded for turning in said staple web threaded hole and includes a pointed lower end for fitting through said hole formed through said movable plate.

* * * * *